United States Patent [19]
Yano et al.

[11] Patent Number: 5,846,810
[45] Date of Patent: Dec. 8, 1998

[54] HUMAN 26S PROTEASOME SUBUNIT COMPONENTS

[75] Inventors: Keiichi Yano, Kawasaki; Motoo Yamasaki, Machida; Keiji Tanaka, Tokushima, all of Japan

[73] Assignee: Kyowa Hakko Kogyo Co. Ltd., Tokyo, Japan

[21] Appl. No.: 506,340

[22] Filed: Jul. 24, 1995

[30] Foreign Application Priority Data

Oct. 28, 1994 [JP] Japan ................................. 6-264810

[51] Int. Cl.$^6$ .......................... C12N 1/21; C12N 15/55; C12N 15/12; C12N 15/63
[52] U.S. Cl. .................. 435/252.3; 435/325; 435/320.1; 435/172.3; 435/69.1; 435/252.33; 536/23.2; 536/23.1; 536/23.5
[58] Field of Search ................. 536/23.2, 23.5, 536/23.1; 435/252.3, 325, 320.1, 172.3, 69.1, 252.33

[56] References Cited

FOREIGN PATENT DOCUMENTS 5-268957 10/1993 Japan .
5-292964 11/1993 Japan .
5-317059 12/1993 Japan .

OTHER PUBLICATIONS

K. Kominami et al., "Nin 1p, a Regulatory Subunit of the 26S Proteasome is Necessary for Activation of Cdc28p Kinase of *Saccharomyces cerevisiae*", EBMO J. 14(13): 3105–3115, Jul. 1995.

GENBANK Locus NO. R16468, Apr. 1995.
GENBANK Locus No. R14974, Apr. 1995.
GENBANK Locus No. T87547, Mar. 1994.
GENBANK Locus No. T87548, Mar. 1995.
GENBANK Locus No. T10004, Apr. 1994.
GENBANK Locus No. R48899, May 1995.
GENBANK Locus No. R48792, May 1995.
Jikken Igaku, vol. 11, No. 20 (1993) 97–102.
Experimental Cell Research, 211 (1994) 203–211.
Experimental Cell Research, 200 (1992) 48–57.
Certificate of Application for Exemption of Application for Lack of Novelty (English translation).
J. Biol. Chem., vol. 269, No. 5 (1994) 3539–47.
J. Biol. Chem., vol. 269, No. 33 (1994) 20878–84.

*Primary Examiner*—Rebecca E. Prouty
*Attorney, Agent, or Firm*—Fitzpatrick, Cella, Harper & Scinto

[57] ABSTRACT

Provided are P112 protein and P31 protein which proteins are among proteins constituting human 26S proteasome, DNAs encoding the proteins, vectors into which the DNAs are inserted and cells carrying the vectors.

The proteins of the present invention are useful not only for elucidating the function of the human 26S proteasome but also for the diagnosis or therapy of various diseases.

12 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 953 amino acids
        ( B ) TYPE: amino acid
        ( D ) TOPOLOGY: linear     ( i i ) MOLECULE TYPE: peptide     ( v i ) ORIGINAL SOURCE:
        ( A ) ORGANISM: human
        ( G ) CELL TYPE: human hepatic carcinoma cell strain HepG2

( x i ) SEQUENCE DESCRIPTION: SEQ ID NO:1:

```
Met Ile Thr Ser Ala Ala Gly Ile Ile Ser Leu Leu Asp Glu Asp Glu
 1               5                  10                  15

Pro Gln Leu Lys Glu Phe Ala Leu His Lys Leu Asn Ala Val Val Asn
                20                  25                  30

Asp Phe Trp Ala Glu Ile Ser Glu Ser Val Asp Lys Ile Glu Val Leu
            35                  40                  45

Tyr Glu Asp Glu Gly Phe Arg Ser Arg Gln Phe Ala Ala Leu Val Ala
        50                  55                  60

Ser Lys Val Phe Tyr His Leu Gly Ala Phe Glu Glu Ser Leu Asn Tyr
65                  70                  75                  80

Ala Leu Gly Ala Arg Asp Leu Phe Asn Val Asn Asp Asn Ser Glu Tyr
                85                  90                  95

Val Glu Thr Ile Ile Ala Lys Cys Ile Asp His Tyr Thr Lys Gln Cys
            100                 105                 110

Val Glu Asn Ala Asp Leu Pro Glu Gly Glu Lys Lys Pro Ile Asp Gln
        115                 120                 125

Arg Leu Glu Gly Ile Val Asn Lys Met Phe Gln Arg Cys Leu Asp Asp
    130                 135                 140

His Lys Tyr Lys Gln Ala Ile Gly Ile Ala Leu Glu Thr Arg Arg Leu
145                 150                 155                 160

Asp Val Phe Glu Lys Thr Ile Leu Glu Ser Asn Asp Val Pro Gly Met
                165                 170                 175

Leu Ala Tyr Ser Leu Lys Leu Cys Met Ser Leu Met Gln Asn Lys Gln
            180                 185                 190

Phe Arg Asn Lys Val Leu Arg Val Leu Val Lys Ile Tyr Met Asn Leu
        195                 200                 205

Glu Lys Pro Asp Phe Ile Asn Val Cys Gln Cys Leu Ile Phe Leu Asp
    210                 215                 220

Asp Pro Gln Ala Val Ser Asp Ile Leu Glu Lys Leu Val Lys Glu Asp
225                 230                 235                 240

Asn Leu Leu Met Ala Tyr Gln Ile Cys Phe Asp Leu Tyr Glu Ser Ala
                245                 250                 255

Ser Gln Gln Phe Leu Ser Ser Val Ile Gln Asn Leu Arg Thr Val Gly
            260                 265                 270

Thr Pro Ile Ala Ser Val Pro Gly Ser Thr Asn Thr Gly Thr Val Pro
```

|     |     |     |     |     | 275 |     |     |     |     | 280 |     |     |     |     | 285 |     |     |
| --- | --- | --- | --- | --- | --- | --- | --- | --- | --- | --- | --- | --- | --- | --- | --- | --- | --- |
| Gly | Ser | Glu | Lys | Asp | Ser | Asp | Ser | Met | Glu | Thr | Glu | Lys | Thr | Ser |
|     | 290 |     |     |     |     | 295 |     |     |     |     | 300 |     |     |     |
| Ser | Ala | Phe | Val | Gly | Lys | Thr | Pro | Glu | Ala | Ser | Pro | Glu | Pro | Lys | Asp |
| 305 |     |     |     |     | 310 |     |     |     |     | 315 |     |     |     |     | 320 |
| Gln | Thr | Leu | Lys | Met | Ile | Lys | Ile | Leu | Ser | Gly | Met | Ala | Ile | Glu |
|     |     |     |     | 325 |     |     |     |     | 330 |     |     |     |     | 335 |
| Leu | His | Leu | Gln | Phe | Leu | Ile | Arg | Asn | Asn | Thr | Asp | Leu | Met | Ile |
|     |     |     | 340 |     |     |     |     | 345 |     |     |     | 350 |     |     |
| Leu | Lys | Asn | Thr | Lys | Asp | Ala | Val | Arg | Asn | Ser | Val | Cys | His | Thr | Ala |
|     |     |     | 355 |     |     |     | 360 |     |     |     |     | 365 |     |     |     |
| Thr | Val | Ile | Ala | Asn | Ser | Phe | Met | His | Cys | Gly | Thr | Thr | Ser | Asp | Gln |
|     | 370 |     |     |     |     | 375 |     |     |     |     | 380 |     |     |     |     |
| Phe | Leu | Arg | Asp | Asn | Leu | Glu | Trp | Leu | Ala | Arg | Ala | Thr | Asn | Trp | Ala |
| 385 |     |     |     |     | 390 |     |     |     |     | 395 |     |     |     |     | 400 |
| Lys | Phe | Thr | Ala | Thr | Ala | Ser | Leu | Gly | Val | Ile | His | Lys | Gly | His | Glu |
|     |     |     |     | 405 |     |     |     |     | 410 |     |     |     |     | 415 |     |
| Lys | Glu | Ala | Leu | Gln | Leu | Met | Ala | Thr | Tyr | Leu | Pro | Lys | Asp | Thr | Ser |
|     |     |     | 420 |     |     |     |     | 425 |     |     |     |     | 430 |     |     |
| Pro | Gly | Ser | Ala | Tyr | Gln | Glu | Gly | Gly | Leu | Tyr | Ala | Leu | Gly | Leu |
|     |     | 435 |     |     |     |     | 440 |     |     |     |     | 445 |     |     |
| Ile | His | Ala | Asn | His | Gly | Gly | Asp | Ile | Ile | Asp | Tyr | Leu | Leu | Asn | Gln |
|     | 450 |     |     |     |     | 455 |     |     |     |     | 460 |     |     |     |     |
| Leu | Lys | Asn | Ala | Ser | Asn | Asp | Ile | Val | Arg | His | Gly | Gly | Ser | Leu | Gly |
| 465 |     |     |     |     | 470 |     |     |     |     | 475 |     |     |     |     | 480 |
| Leu | Gly | Leu | Ala | Ala | Met | Gly | Thr | Ala | Arg | Gln | Asp | Val | Tyr | Asp | Leu |
|     |     |     |     | 485 |     |     |     |     | 490 |     |     |     |     | 495 |     |
| Leu | Lys | Thr | Asn | Leu | Tyr | Gln | Asp | Asp | Ala | Val | Thr | Gly | Glu | Ala | Ala |
|     |     |     | 500 |     |     |     |     | 505 |     |     |     |     | 510 |     |     |
| Gly | Leu | Ala | Leu | Gly | Leu | Val | Met | Leu | Gly | Ser | Lys | Asn | Ala | Gln | Ala |
|     |     |     | 515 |     |     |     | 520 |     |     |     |     | 525 |     |     |     |
| Ile | Glu | Asp | Met | Val | Gly | Tyr | Ala | Gln | Glu | Thr | Gln | His | Glu | Lys | Ile |
|     |     | 530 |     |     |     |     | 535 |     |     |     |     | 540 |     |     |     |
| Leu | Arg | Gly | Leu | Ala | Val | Gly | Ile | Ala | Leu | Val | Met | Tyr | Gly | Arg | Met |
| 545 |     |     |     |     | 550 |     |     |     |     | 555 |     |     |     |     | 560 |
| Glu | Glu | Ala | Asp | Ala | Leu | Ile | Glu | Ser | Leu | Cys | Arg | Asp | Lys | Asp | Pro |
|     |     |     |     | 565 |     |     |     |     | 570 |     |     |     |     | 575 |     |
| Ile | Leu | Arg | Arg | Ser | Gly | Met | Tyr | Thr | Val | Ala | Met | Ala | Tyr | Cys | Gly |
|     |     |     | 580 |     |     |     |     | 585 |     |     |     |     | 590 |     |     |
| Ser | Gly | Asn | Asn | Lys | Ala | Ile | Arg | Arg | Leu | Leu | His | Val | Ala | Val | Ser |
|     |     | 595 |     |     |     |     | 600 |     |     |     |     | 605 |     |     |     |
| Asp | Val | Asn | Asp | Asp | Val | Arg | Ser | Ala | Ala | Val | Glu | Ser | Leu | Gly | Phe |
|     | 610 |     |     |     |     | 615 |     |     |     |     | 620 |     |     |     |     |
| Ile | Leu | Phe | Arg | Thr | Pro | Glu | Gln | Cys | Pro | Ser | Val | Val | Ser | Leu | Leu |
| 625 |     |     |     |     | 630 |     |     |     |     | 635 |     |     |     |     | 640 |
| Ser | Glu | Ser | Tyr | Asn | Pro | His | Val | Arg | Tyr | Gly | Ala | Ala | Met | Ala | Leu |
|     |     |     |     | 645 |     |     |     |     | 650 |     |     |     |     | 655 |     |
| Gly | Ile | Cys | Cys | Ala | Gly | Thr | Gly | Asn | Lys | Glu | Ala | Ile | Asn | Leu | Leu |
|     |     |     | 660 |     |     |     |     | 665 |     |     |     |     | 670 |     |     |
| Glu | Pro | Met | Thr | Asn | Asp | Pro | Val | Asn | Tyr | Val | Arg | Gln | Gly | Ala | Leu |
|     |     |     | 675 |     |     |     |     | 680 |     |     |     |     | 685 |     |     |
| Ile | Ala | Ser | Ala | Leu | Ile | Met | Ile | Gln | Gln | Thr | Glu | Ile | Thr | Cys | Pro |
|     |     |     | 690 |     |     |     |     | 695 |     |     |     |     | 700 |     |     |

| Lys | Val | Asn | Gln | Phe | Arg | Gln | Leu | Tyr | Ser | Lys | Val | Ile | Asn | Asp | Lys |
| --- | --- | --- | --- | --- | --- | --- | --- | --- | --- | --- | --- | --- | --- | --- | --- |
| 705 | | | | | 710 | | | | 715 | | | | | | 720 |
| His | Asp | Asp | Val | Met | Ala | Lys | Phe | Gly | Ala | Ile | Leu | Ala | Gln | Gly | Ile |
| | | | | 725 | | | | 730 | | | | | 735 | | |
| Leu | Asp | Ala | Gly | Gly | His | Asn | Val | Thr | Ile | Ser | Leu | Gln | Ser | Arg | Thr |
| | | | 740 | | | | | 745 | | | | | 750 | | |
| Gly | His | Thr | His | Met | Pro | Ser | Val | Val | Gly | Val | Leu | Val | Phe | Thr | Gln |
| | | 755 | | | | | 760 | | | | | 765 | | | |
| Phe | Trp | Phe | Trp | Phe | Pro | Leu | Ser | His | Phe | Leu | Ser | Leu | Ala | Tyr | Thr |
| | 770 | | | | | 775 | | | | | 780 | | | | |
| Pro | Thr | Cys | Val | Ile | Gly | Leu | Asn | Lys | Asp | Leu | Lys | Met | Pro | Lys | Val |
| 785 | | | | | 790 | | | | 795 | | | | | | 800 |
| Gln | Tyr | Lys | Ser | Asn | Cys | Lys | Pro | Ser | Thr | Phe | Ala | Tyr | Pro | Ala | Pro |
| | | | | 805 | | | | | 810 | | | | | 815 | |
| Leu | Glu | Val | Pro | Lys | Glu | Lys | Glu | Lys | Glu | Lys | Val | Ser | Thr | Ala | Val |
| | | | 820 | | | | | 825 | | | | | 830 | | |
| Leu | Ser | Ile | Thr | Ala | Lys | Ala | Lys | Lys | Glu | Lys | Glu | Lys | Glu | Lys |
| | | 835 | | | | 840 | | | | | 845 | | | |
| Lys | Glu | Glu | Glu | Lys | Met | Glu | Val | Asp | Glu | Ala | Lys | Lys | Glu | Glu |
| | 850 | | | | | 855 | | | | 860 | | | | |
| Lys | Glu | Lys | Lys | Lys | Glu | Pro | Glu | Pro | Asn | Phe | Gln | Leu | Leu | Asp | Asn |
| 865 | | | | | 870 | | | | 875 | | | | | | 880 |
| Pro | Ala | Arg | Val | Met | Pro | Ala | Gln | Leu | Lys | Val | Leu | Thr | Met | Pro | Glu |
| | | | | 885 | | | | | 890 | | | | | 895 | |
| Thr | Cys | Arg | Tyr | Gln | Pro | Phe | Lys | Pro | Leu | Ser | Ile | Gly | Gly | Ile | Ile |
| | | | 900 | | | | | 905 | | | | | 910 | | |
| Ile | Leu | Lys | Asp | Thr | Ser | Glu | Asp | Ile | Glu | Glu | Leu | Val | Glu | Pro | Val |
| | | 915 | | | | | 920 | | | | | 925 | | | |
| Ala | Ala | His | Gly | Pro | Lys | Ile | Glu | Glu | Glu | Glu | Gln | Glu | Pro | Glu | Pro |
| | | 930 | | | | | 935 | | | | | 940 | | | |
| Pro | Glu | Pro | Phe | Glu | Tyr | Ile | Asp | Asp |
| 945 | | | | | 950 | | | 953 |

(2) INFORMATION FOR SEQ ID NO:2:

(i) SEQUENCE CHARACTERISTICS:
        (A) LENGTH: 2859 base pairs
        (B) TYPE: nucleic acid
        (C) STRANDEDNESS: single
        (D) TOPOLOGY: linear     (ii) MOLECULE TYPE: cDNA to mRNA     (vi) ORIGINAL SOURCE:
        (A) ORGANISM: human
        (G) CELL TYPE: human hepatic carcinoma cell strain HepG2

(xi) SEQUENCE DESCRIPTION: SEQ ID NO:2:

| | | | | | |
| --- | --- | --- | --- | --- | --- |
| ATGATCACCT | CGGCCGCTGG | AATTATTTCT | CTTCTGGATG | AAGATGAACC | ACAGCTTAAG | 60 |
| GAATTTGCAC | TACACAAATT | GAATGCAGTT | GTTAATGACT | TCTGGGCAGA | AATTTCCGAG | 120 |
| TCCGTAGACA | AAATAGAGGT | TTTATACGAA | GATGAAGGTT | TCCGGAGTCG | GCAGTTTGCA | 180 |
| GCCTTAGTGG | CATCTAAAGT | ATTTTATCAC | CTGGGGGCTT | TTGAGGAGTC | TCTGAATTAT | 240 |
| GCTCTTGGAG | CAAGGGACCT | CTTCAATGTC | AATGATAACT | CTGAATATGT | GGAAACTATT | 300 |
| ATAGCAAAAT | GCATTGATCA | CTACACCAAA | CAATGTGTGG | AAAATGCAGA | TTTGCCTGAA | 360 |
| GGAGAAAAAA | AACCAATTGA | CCAGAGATTG | GAAGGCATCG | TAAATAAAAT | GTTCCAGCGA | 420 |
| TGTCTAGATG | ATCACAAGTA | TAAACAGGCT | ATTGGCATTG | CTCTGGAGAC | ACGAAGACTG | 480 |

-continued

```
GACGTCTTTG AAAAGACCAT ACTGGAGTCG AATGATGTCC CAGGAATGTT AGCTTATAGC    540
CTTAAGCTCT GCATGTCTTT AATGCAGAAT AAACAGTTTC GGAATAAAGT ACTAAGAGTT    600
CTAGTTAAAA TCTACATGAA CTTGGAGAAA CCTGATTTCA TCAATGTTTG TCAGTGCTTA    660
ATTTTCTTAG ATGATCCTCA GGCTGTGAGT GATATCTTAG AGAAACTGGT AAAGGAAGAC    720
AACCTCCTGA TGGCATATCA GATTTGTTTT GATTTGTATG AAAGTGCTAG CCAGCAGTTT    780
TTGTCATCTG TAATCCAGAA TCTTCGAACT GTTGGCACCC CTATTGCTTC TGTGCCTGGA    840
TCCACTAATA CGGGTACTGT TCCGGGATCA GAGAAGACA GTGACTCGAT GGAAACAGAA    900
GAAAAGACAA GCAGTGCATT TGTAGGAAAG ACACCAGAAG CCAGTCCAGA GCCTAAGGAC    960
CAGACTTTGA AAATGATTAA AATTTTAAGT GGTGAAATGG CTATTGAGTT ACATCTGCAG   1020
TTCTTAATAC GAAACAATAA TACAGACCTC ATGATTCTAA AAAACACAAA GGATGCAGTA   1080
CGGAATTCTG TATGTCATAC TGCAACCGTT ATAGCAAACT CTTTTATGCA CTGTGGGACA   1140
ACCAGTGACC AGTTTCTTAG AGATAATTTG GAATGGTTAG CCAGAGCCAC TAACTGGGCA   1200
AAATTTACTG CTACAGCCAG TTTGGGTGTA ATTCATAAGG GTCATGAAAA AGAAGCATTA   1260
CAGTTAATGG CAACATACCT TCCCAAGGAT ACTTCTCCAG GATCAGCCTA TCAGGAAGGT   1320
GGAGGTCTCT ATGCACTAGG TCTTATTCAT GCCAATCATG GTGGTGATAT AATTGACTAT   1380
CTGCTTAATC AGCTTAAGAA CGCCAGCAAT GATATCGTTA GACACGGTGG CAGTCTGGGC   1440
CTTGGTTTGG CAGCCATGGG AACTGCACGT CAAGATGTTT ATGATTGCT AAAAACAAAC    1500
CTTTATCAGG ATGATGCAGT AACAGGGGAA GCAGCTGGCC TGGCCCTAGG TTTGGTTATG   1560
TTGGGCTCTA AAAATGCTCA GGCTATTGAG GACATGGTTG GTTATGCACA AGAAACTCAA   1620
CATGAGAAGA TTCTGCGTGG TCTTGCAGTT GGCATAGCTT TAGTAATGTA TGGGAGGATG   1680
GAAGAGGCTG ATGCTCTCAT TGAATCTCTC TGTCGTGACA AGGACCCAAT TCTTCGAAGG   1740
TCTGGAATGT ATACTGTAGC CATGGCTTAT TGTGGCTCTG GTAACAACAA AGCAATTCGA   1800
CGCCTGCTAC ATGTGGCTGT AAGTGATGTG AATGATGATG TCAGGAGTGC AGCAGTAGAA   1860
TCACTTGGGT TCATTCTATT CAGAACCCCT GAACAGTGCC CAAGTGTTGT CTCTTTGTTG   1920
TCAGAGAGTT ACAACCCTCA TGTGCGCTAC GGAGCTGCAA TGGCCTTGGG GATATGCTGT   1980
GCTGGTACAG GAAACAAGGA AGCCATTAAT TTGCTAGAAC CAATGACAAA CGACCCCGTG   2040
AACTACGTGA GGCAAGGGGC ACTCATAGCT TCAGCTCTCA TCATGATCCA GCAGACTGAA   2100
ATCACTTGTC CAAAGGTGAA TCAGTTCAGA CAGCTGTATT CCAAAGTCAT CAATGATAAG   2160
CATGATGATG TCATGGCCAA GTTTGGCGCT ATTCTGGCCC AGGGCATACT GGATGCAGGT   2220
GGTCATAATG TCACAATCTC CTTGCAGTCC AGGACTGGGC ATACTCATAT GCCTTCTGTG   2280
GTTGGCGTCC TTGTATTTAC CCAGTTTTGG TTCTGGTTTC CTCTTTCACA CTTCCTGTCA   2340
TTGGCTTATA CCCCTACCTG TGTCATTGGC CTTAACAAGG ACTTAAAGAT GCCGAAAGTT   2400
CAGTATAAAT CGAACTGTAA ACCATCCACA TTTGCATATC CTGCCCCTCT GGAAGTACCA   2460
AAAGAAAAAG AAAAGGAAAA GGTTTCTACT GCTGTATTAT CTATAACTGC CAAGGCTAAA   2520
AAGAAGGAAA AAGAAAAGGA AAAAAAGGAG GAGGAGAAAA TGGAAGTGGA TGAGGCAGAG   2580
AAAAGGAGG AAAAAGAGAA GAAAAAGAA CCTGAGCCAA ACTTCCAGTT ATTGGATAAC   2640
CCAGCCCGAG TTATGCCTGC CCAGCTTAAG GTCCTAACCA TGCCGGAGAC CTGTAGATAC   2700
CAGCCTTTCA AACCACTCTC TATTGGAGGC ATCATCATTC TGAAGGATAC CAGTGAAGAC   2760
ATTGAGGAGC TGGTGGAACC TGTGGCAGCA CATGGCCCAA AAATCGAGGA GGAGGAACAA   2820
GAGCCAGAAC CCCCAGAACC ATTTGAGTAT ATTGATGAT                          2859
```

( 2 ) INFORMATION FOR SEQ ID NO:3:

( i ) SEQUENCE CHARACTERISTICS:
        ( A ) LENGTH: 257 amino acids
        ( B ) TYPE: amino acid
        ( D ) TOPOLOGY: linear     ( i i ) MOLECULE TYPE: peptide     ( v i ) ORIGINAL SOURCE:
        ( A ) ORGANISM: human
        ( G ) CELL TYPE: human hepatic carcinoma cell strain HepG2

( x i ) SEQUENCE DESCRIPTION: SEQ ID NO:3:

```
Met Tyr Glu Gln Leu Lys Gly Glu Trp Asn Arg Lys Ser Pro Asn Leu
 1               5                  10                  15
Ser Lys Cys Gly Glu Glu Leu Gly Arg Leu Lys Leu Val Leu Leu Glu
            20                  25                  30
Leu Asn Phe Leu Pro Thr Thr Gly Thr Lys Leu Thr Lys Gln Gln Leu
        35                  40                  45
Ile Leu Ala Arg Asp Ile Leu Glu Ile Gly Ala Gln Trp Ser Ile Leu
    50                  55                  60
Arg Lys Asp Ile Pro Ser Phe Glu Arg Tyr Met Ala Gln Leu Lys Cys
65                  70                  75                  80
Tyr Tyr Phe Asp Tyr Lys Glu Gln Leu Pro Glu Ser Ala Tyr Met His
                85                  90                  95
Gln Leu Leu Gly Leu Asn Leu Leu Phe Leu Leu Ser Gln Asn Arg Val
            100                 105                 110
Ala Glu Phe His Thr Glu Leu Glu Arg Leu Pro Ala Lys Asp Ile Gln
        115                 120                 125
Thr Asn Val Tyr Ile Lys His Pro Val Ser Leu Glu Gln Tyr Leu Met
    130                 135                 140
Glu Gly Ser Tyr Asn Lys Val Phe Leu Ala Lys Gly Asn Ile Pro Ala
145                 150                 155                 160
Glu Ser Tyr Thr Phe Phe Ile Asp Ile Leu Leu Asp Thr Ile Arg Asp
                165                 170                 175
Glu Ile Ala Gly Cys Ile Glu Lys Ala Tyr Glu Lys Ile Leu Phe Thr
            180                 185                 190
Glu Ala Thr Arg Ile Leu Phe Phe Asn Thr Pro Lys Lys Met Thr Asp
        195                 200                 205
Tyr Ala Lys Lys Arg Gly Trp Val Leu Gly Pro Asn Asn Tyr Tyr Ser
    210                 215                 220
Phe Ala Ser Gln Gln Gln Lys Pro Glu Asp Thr Thr Ile Pro Ser Thr
225                 230                 235                 240
Glu Leu Ala Lys Gln Val Ile Glu Tyr Ala Arg Gln Leu Glu Met Ile
                245                 250                 255
Val
257
```

( 2 ) INFORMATION FOR SEQ ID NO:4:

( i ) SEQUENCE CHARACTERISTICS:
        ( A ) LENGTH: 771 base pairs
        ( B ) TYPE: nucleic acid
        ( C ) STRANDEDNESS: single
        ( D ) TOPOLOGY: linear     ( i i ) MOLECULE TYPE: cDNA to mRNA     ( v i ) ORIGINAL SOURCE:

(A) ORGANISM: human
(G) CELL TYPE: human hepatic carcinoma cell strain HepG2

(xi) SEQUENCE DESCRIPTION: SEQ ID NO:4:

```
ATGTACGAGC  AACTCAAGGG  CGAGTGGAAC  CGTAAAAGCC  CCAATCTTAG  CAAGTGCGGG   60
GAAGAGCTGG  GTCGACTCAA  GCTAGTTCTT  CTGGAGCTCA  ACTTCTTGCC  AACCACAGGG  120
ACCAAGCTGA  CCAAACAGCA  GCTAATTCTG  GCCCGTGACA  TACTGGAGAT  CGGGGCCCAA  180
TGGAGCATCC  TACGCAAGGA  CATCCCCTCC  TTCGAGCGCT  ACATGGCCCA  GCTCAAATGC  240
TACTACTTTG  ATTACAAGGA  GCAGCTCCCC  GAGTCAGCCT  ATATGCACCA  GCTCTTGGGC  300
CTCAACCTCC  TCTTCCTGCT  GTCCCAGAAC  CGGGTGGCTG  AGTTCCACAC  GGAGTTGGAG  360
CGGCTGCCTG  CCAAGGACAT  ACAGACCAAT  GTCTACATCA  AGCACCAGT  GTCCCTGGAG  420
CAATACCTGA  TGGAGGGCAG  CTACAACAAA  GTGTTCCTGG  CCAAGGGTAA  CATCCCCGCC  480
GAGAGCTACA  CCTTCTTCAT  TGACATCCTG  CTCGACACTA  TCAGGGATGA  GATCGCTGGG  540
TGCATCGAGA  AGGCCTACGA  GAAAATCCTT  TTCACTGAGG  CCACCCGGAT  CCTCTTCTTC  600
AACACACCCA  AAAGATGAC   AGACTACGCC  AAGAAGCGAG  GGTGGGTCCT  GGGCCCCAAC  660
AACTACTACA  GTTTTGCCAG  CCAGCAGCAG  AAGCCGGAAG  ACACCACCAT  TCCCTCCACA  720
GAACTGGCCA  AACAGGTCAT  CGAGTATGCC  CGGCAGCTGG  AGATGATCGT  C           771
```

HUMAN 26S PROTEASOME SUBUNIT COMPONENTS

BACKGROUND OF THE INVENTION

The present invention relates to proteins constituting human 26S proteasome which is a human intracellular protease.

The proteins of the present invention are useful not only for elucidating the function of human 26S proteasome but also for diagnosis or therapy of various diseases.

A proteasome is a multi-functional protease which is widely spread in eucaryotes ranging from yeasts to human beings, and which energy-dependently decomposes ubiquitin-bound proteins within cells. The enzyme includes 20S proteasome composed of various components having a molecular weight of from 21 to 31 kilodaltons, and a group of PA700 regulatory proteins composed of various subunits having a molecular weight of from 30 to 112 kilodaltons and a sedimentation coefficient of 22S; the enzyme forms a giant molecule having a molecular weight of approximately 2,000,000 daltons and a sedimentation coefficient of 26S as a whole [Rechesteiner, M., et al., J. Biol., Chem., 268, 6065–6068 (1993), Yoshimura, T., et al., J. Struct. Biol., 111, 200–211 (1993), Tanaka, K., et al., New Biologist, 4, 173–187 (1992)]. The structure and functions of the enzyme have not yet been completely analyzed through analysis of the structure and functions thereof. The investigations over analysis of the functions of the proteasome using yeasts and mice reveal the following.

An elucidation of the intracellular energy-dependent protein decomposition mechanism started from screening of a protein by binding the protein to ubiquitin. However, it has been clarified that an ATP-dependent activity of decomposing the ubiquitin-bound protein is not present in 20S proteasome but in 26S proteasome [Chu-Ping et al., J. Biol., Chem., 269, 3539–3547 (1994)], and human 26S proteasome of the present invention is useful for elucidating the energy-dependent protein decomposition mechanism. Most factors participating in regulation of a cell cycle generally have a short half-life and undergo strict quantitative control. In practice, it has been clarified that Mos, Myc and Fos which are oncogene products are decomposed with 26S proteasome which is dependent on energy and ubiquitin [Ishida, N., et al., FEBS Lett., 324, 345–348 (1993), Hershko, A., and Ciechanover, A., Annu. Rev. Biochem., 61, 761–807 (1992)], and the significance of the proteasome in the cell cycle control is currently being perceived.

Further, the significance of the proteasome in the immune system is also perceived. It is suggested that the proteasome may positively be related with presentation of class I major histocompatibility complex antigen [Michalek MT., et al., Nature, 363, 552–554 (1993)]. Still further, it is reported that the ubiquitin-bound protein is abnormally accumulated in brains of the patients who suffer from Alzheimer's disease [Kitaguchi, N., et al., Nature, 331, 530–532 (1988)]. From this phenomenon, it is suggested that the proteasome may be related with the Alzheimer's disease. The proteasome has thus the various functions, and is therefore useful for the diagnosis or therapy of various diseases.

The main function of 26S proteasome lies in an activity of decomposing the ubiquitin-bound protein. It has been elucidated that the oncogene products including c-Myc or the cell cycle-associated gene products such as cyclin are decomposed in the ubiquitin-dependent pathway. Further, the proteasome gene is abnormally expressed in hepatic carcinoma cells, renal carcinoma cells, leukemia cells and the like in comparison to normal cells [Kanayama, H., et al., Cancer Res., 51, 6677–6685 (1991)]. It is observed that the proteasome is abnormally accumulated in the tumor cell nucleus. Accordingly, the components of the proteasome in the present invention are expected to be useful for elucidating the mechanism of malignant alteration of these cells or for the diagnosis or therapy of tumors. Further, it is known that the expression of the proteasome is induced by interferon γ, etc. and the structural diversity of proteasome may be related to antigen presentation in the cell [Aki, M., et al., J. Biochem., 115, 257–269 (1994)]. Consequently, the components of the proteasome can be expected to help elucidate the mechanism of presenting the antigen in the immune system or to help develop an immunosuppresant.

Still further, the proteasome is considered to be deeply related with ubiquitin which is abnormally accumulated in brains of the patients who suffer from the Alzheimer's disease. Thus, the components of the human proteasome of the present invention are useful for elucidating the cause of the Alzheimer's disease or for therapy of the Alzheimer's disease.

The proteasome which is expected to be the polyfunctional enzyme as mentioned above can further be used in the diagnosis of various diseases through immunoassay by producing antibodies against the components of proteasome.

Proteins having characteristics of the human 26S proteasome in the present invention are disclosed in Japanese Published Unexamined Patent Application No. 292,964/93, and proteins constituting a rat proteasome are disclosed in Japanese Published Unexamined Patent Application Nos. 268,957/93 and 317,059/93. However, the components of the human 26S proteasome of the present invention are not yet known.

SUMMARY OF THE INVENTION

The object of the present invention is to provide P112 protein and P31 protein among proteins constituting human 26S proteasome, DNAs encoding these proteins, vectors into which these DNAs are inserted, and cells carrying these vectors.

The present invention relates to human 26S proteasome component P112 protein having an amino acid sequence represented by Sequence No. 1 and human 26S proteasome component P31 protein having an amino acid sequence represented by Sequence No. 3, DNAs encoding these proteins, vectors into which these DNAs are inserted, and cells carrying these vectors. The human 26S proteasome component P112 protein and human 26S proteasome component P31 of the present invention also include polypeptides in which methionine is not present in the N-terminals of the amino acid sequences represented by Sequence Nos. 1 and 3, respectively, and polypeptides in which part or the whole of signal peptide sequence of the human proteasome component P112 protein and P31 protein are bound to the N-terminals of the amino acid sequences, respectively.

It is possible that part of DNA encoding a polypeptide is changed by spontaneous or artificial mutation without having a great influence on the main activity of the polypeptide. The present invention also includes a polypeptide corresponding to such an homologous mutant.

The proteins of the present invention can be obtained by being isolated from internal organs or cell strains of various animals including human being or by a method based on peptide synthesis. However, a process according to a recombinant DNA technology is preferred. The process for producing the proteins of the present invention according to the recombinant DNA technology is described below.

DNAs encoding P112 protein and P31 protein which are components of the human 26S proteasome are produced as follows.

First, phages containing DNAs encoding P112 protein and P31 protein are isolated from a cDNA library of cytoplasmic fractions of internal organs such as human kidney, liver, heart, brain, lung and thymus and cell strains such as human hepatic carcinoma cell strains [for example, HepG2 cell strain (ATCC HB8065)] and human renal cell strains that produce human 26S proteasome components by plaque hybridization using as probes DNA fragments which are synthesized by RT-PCR [combined reverse transcription-polymerase chain reaction, Science, 241, 708–712 (1988)] based on amino acid sequences of portions of a bovine proteasome corresponding to P112 protein and P31 protein [DeMartino, GN., et al., J. Biol., Chem., 269, 20878–20884 (1994)].

A process for preparing the above-mentioned cDNA library is described below.

The whole RNA is obtained from human HepG2 cell which is a cell to produce human 26S proteasome by a guanidine/cesium chloride method or a guanidine thiocyanate method. Then, mRNA encoding the protein of the present invention from the whole RNA is purified by a column method using an oligo dT cellulose or a batch method. Using the obtained mRNA as a template, cDNA is then synthesized with a reverse transcriptase by the Okayama-Berg method [Mol. Cell. Biol., 2, 161–170 (1982)] or the Gubler-Hoffman method [Gene, 25, 263–269 (1983)]. The resulting cDNA is inserted into a plasmid or phase vector to prepare the cDNA library.

Any plasmid or phage vector into which the cDNA is to be inserted is available if the CDNA of the present invention is replicated and retained in a host cell. Examples thereof include plasmid vectors such as pBR322 and pC119, and phage vectors such as λgt10.

As the method of inserting the cDNA into the plasmid vectors, the method of the Sambrook, et al [EMBO J., 4, 91–103 (1983)] is used, and as the method of inserting the cDNA into the phage vector, the method of Hyunh, T. V., et al [A Practical Approach (compiled by D. M. Glover), 1, 49, IRL Press, Oxford] is used.

The above-mentioned plasmid can be introduced into a suitable host cell such as *Escherichia coli* and *Bacillus*. The phage vector can be introduced into a host cell which is proliferated by an in vitro packaging method.

The CDNA which encodes the component of the human proteasome is selected from the resulting cDNAs by plaque hybridization using a labeled probe or by colony hybridization.

A DNA which is used as the probe in the above-mentioned hybridization procedure may be any DNA which is hybridized with the DNA which encodes P112 protein or P31 protein which is the component of 26S proteasome of the present invention. Also available are cDNA, genomic DNA and chemically synthesized DNA encoding an oligonucleotide formed on the basis of the amino acid sequence of the component, and partial DNAs of the DNA. It is also possible to select suitable sequences according to base sequences of components as determined with mice or yeasts other than human beings. The plasmid or phage vectors containing the cDNA encoding P31 protein which is the component of the human 26S proteasome of the present invention includes P31 plasmid. The plasmid or phage vector containing the cDNA encoding P112 protein which is the component of the human 26S proteasome of the present invention includes P112 plasmid. *E. coli* P31 which is an *Escherichia coli* carrying P31 plasmid and *E. coli* P112 which is an *Escherichia coli* containing P112 plasmid have been deposited under FERM BP-4837 and FERM BP-4838 with the National Institute of Bioscience and Human Technology of the Agency of Industrial Science and Technology as of Oct. 18, 1994. The base sequence of DNA can be determined by the Maxam-Gilbert method or the dideoxy method.

DNAs containing cDNAs encoding P112 protein and P31 protein which are components of the human 26S proteasome of the present invention can also be cloned from genomic DNA libraries of human being, mice, yeasts and the like. Any promoter, terminator and secretion signal that function in a host cell are applicable and obtainable by a known recombination technology. The DNA of the present invention is not necessarily expressed in the above-mentioned direct expression. Also available is a method in which the protein fused with another protein such as β-galactosidase is expressed, and then cleaved with a suitable protease.

The host cell includes eucaryotes such as animal cells, insect cells and yeasts, and procaryotes such as *Escherichia coli* and *Bacillus* if the vector of the present invention can be inserted thereinto and the proteins of the present invention can be produced. The cell carrying the recombinant vector of the present invention can be cultivated also in a usual manner.

The proteins can be isolated from the culture and purified by a combination of known separation procedures such as treatment with a denaturant such as urea or a surfactant, sonication, enzymatic digestion, salting-out, solvent precipitation, dialysis, centrifugation, ultrafiltration, gel filtration, SDS-polyacrylamide gel electrophoresis (SDS-PAGE), isoelectric electrophoresis, ion-exchange chromatography, hydrophobic chromatography, affinity chromatography and reversed-phase chromatography.

In the present invention, amino acids and peptides are abbreviatingly described by the method accepted by Commission on Biochemical Nomenclature of IUPAC-IUB, and for example, the following abbreviations are used.

Incidentally, amino acids include optical isomers. In the present specification and claims, amino acids are L-isomers unless otherwise instructed.

Ala: (A) alanine
Arg: (R) arginine
Asn: (N) asparagine
Asp: (D) aspartic acid
Cys: (C) cysteine
Gln: (Q) glutamine
Glu: (E) glutamic acid
Gly: (G) glycine
His: (H) histidine
Ile: (I) isoleucine
Leu: (L) leucine
Lys: (K) lysine
Met: (M) methionine
Phe: (F) phenylalanine
Pro: (P) proline
Ser: (S) serine
Thr: (T) threonine
Trp: (W) tryptophan
Tyr: (Y) tyrosine
Val: (V) valine Polydeoxyribonucleotides and oligonucleotides are represented by the sequences of deoxyribonucleotides having the following abbreviations.

A: adenine
C: cytosine
G: guanine
T: thymine

The left terminal of the deoxyribonucleotide sequence is 5'-terminal unless otherwise instructed.

The present invention will be illustrated specifically by referring to the following Examples.

EXAMPLE 1

(1) Purification of P112 protein and P31 protein which are components of human 26S proteasome Using approximately 100 g of a fresh human kidney, a human proteasome was purified by column chromatography with Biogel A–1.5m(5×90 cm, made by BioRad Co.), hydroxyapatite (1.5×15 cm, made by BioRad Co.) and Q-Cepharose (1.5×15 cm, made by Pharmacia Co.) and by glycerol density gradient centrifugation according to a method of purifying a human proteasome as described in Japanese Published Unexamined Patent Application No. 292,964/93. The obtained proteasome was subjected to reversed-phase high performance liquid chromatography (HPLC) from a Hitachi L6200 Model HPLC System. Using a Shodex RS Pak D4-613 (0.6×15 cm, manufactured by Showa Denko K. K.) as a column, the gradient elution with the following two solutions was carried out.

First solution: 0.06% trifluoroacetic acid
Second solution:
0.05% trifluoroacetic acid, 70% acetonitrile
Gradient:
(first solution: second solution)=linear concentration gradient from (50:50) to (30:70) for 60 minutes
P112 protein elution concentration:
(first solution: second solution)=(38:62)

P31 protein elution concentration:
(first solution: second solution)=(43:57)

Figure 1:
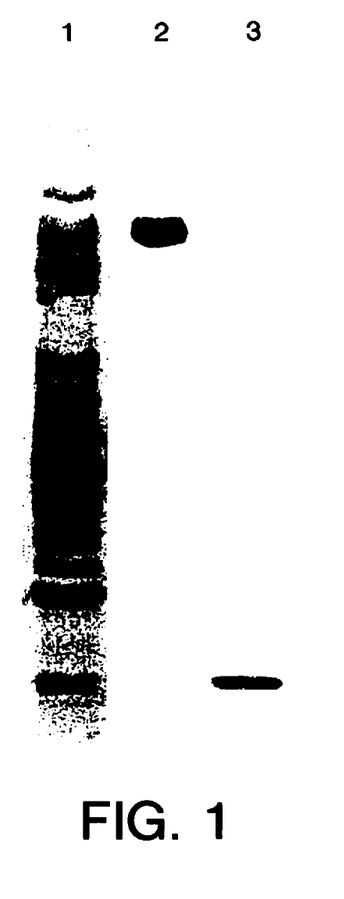
FIG. 1 shows the results of SDS-polyacrylamide gel electrophoresis of human 26S proteasome. Lane 1 shows human 26S proteasome, lane 2 shows component P112 protein, and lane 3 shows component P31 protein.

Part of the thus obtained elution fraction was subjected to 8.5% SDS-polyacrylamide electrophoresis while being reduced with dithiothreitol, whereby P112 protein and P31 protein were isolated and purified. The results of SDS-polyacrylamide gel electrophoresis thereof are shown in FIG. 1.

(2) Preparation of a cDNA library

Human hepatic carcinoma cell strain HepG2 (ATCC HB8065) was incubated in a Dulbecco modified Eagle's medium (DMEM) containing 10% fatal bovine serum. The culture solution was washed with the phosphate buffer and then recovered, and the whole RNA was obtained by a guanidine thioisocyanate method in accordance with the Chirgwin, et al method [Biochemistry, 18, 5294–5299 (1979)]. The whole RNA was additionally bound to an oligo (dT)-latex (Oligo-dT30, made by Takara Shuzo Co., Ltd.) in an oligo (dT) binding buffer [containing 0.5M NaCl, 10 mM tris-HCl (pH 7.5), 1 mM EDTA and 0.1% SDS] at 37° C. for 10 minutes. After the completion of the centrifugation, the supernatant was removed, and the residue was suspended in a washing buffer [containing 0.1M NaCl, 10 mM tris-HCl (pH 7.5), 1 mM EDTA and 0.1% SDS]. The suspension was then recentrifuged to remove the supernatant, thereby removing tRNA and rRNA. Poly(A)$^+$RNA bound to the oligo (dT)-latex was eluted with distilled water at 65° C. for 5 minutes. To the elute were added 1/20 volume of 5M NaCl and 2.5 volumes of ethanol to conduct ethanol precipitation. The precipitate was washed with 70% ethanol to obtain poly(A)$^+$RNA. Using the poly(A)$^+$RNA, single-stranded cDNA which was a template for producing a probe was synthesized with a First-Strand cDNA Synthesis Kit (made by Pharmacia Co.) by the polymerase chain reaction method (PCR method). Using the obtained poly(A)$^+$RNA as a template, double-stranded cDNA having a restriction endonuclease EcoRI cleavage terminal was synthesized by means of a Time Saver cDNA Synthesis Kit (made by Pharmacia Co.) in accordance with the Gubler-Hoffman method [Gene, 25, 263–268 (1983)]. That is, using the poly(A)$^+$RNA as the template, the single-stranded cDNA was synthesized with an oligo (dT)$_{12-18}$ primer and Cloned Murin Reverse Transcriptase, and further the double-stranded cDNA was synthesized with E. coli RNase H and E. coli DNA polymerase. The thus-synthesized double-stranded cDNA was smoothed with a Klenow fragment (DNA polymerase I Large Fragment made by Nippon Gene). Subsequently, EcoRI-Notl adaptor having an EcoRI cleavage terminal was added thereto by means of a T4 DNA ligase. Further, the EcoRI cleavage terminal was phosphorylated with a T4 polynucleotide kinase. Then, packaging of λZAPII was conducted using an EcoRI site (prodigested LAMBDA ZAPII/EcoRI/CIAP CLONING KIT, made by Stratagene) of a multicloning site of λZAPII which is a phage cloning vector. Thereafter, a cDNA library was prepared using E. coli XL1-Blue as a host cell.

(3) Preparation of a probe

The P112 protein obtained in (1) was digested with 1 μg of trypsin in 0.1M tris buffer (pH 7.8) and 2M urea at 37° C. for 8 hours. The obtained partial peptide fragments were separated by reversed-phase HPLC, and the amino acid sequences of the N-terminal thereof were determined and then found to be XNLYQDDAVTGE and XXAIL-AQGILDAG (in which X is an undetermined amino acid). Based on these amino acid sequences, primers of a sense strand: [5'-AAT(T/C)T(T/G)TATCAGGATGATGCTGT(T/G)AC(T/G)GGTGA-3'] and an anti-sense strand: [5'-

CCAGCATC(A/C)AAAATACCCTGAGC(A/C)A(A/G)AAT(A/C)GC-3'] were synthesized. PCR was conducted using the HepG2 cell first-strand cDNA obtained in (2) as a template. As a result, the PCR product of 720 nucleotides was obtained. In order to smooth this PCR product, the product was treated with a Klenow fragment (made by Nippon Gene), and both terminals were phosphorylated with a T4 polynucleotide kinase (made by Nippon Gene). The resulting product was inserted into pBluescriptIIKs (+) vector which had been cleaved with EcoRV by means of a T4 DNA ligase. The amino acid sequence was determined, and it was consequently found that the PCR product showed high homology with the amino acid sequence of bovine proteasome P112 protein. Accordingly, this fragment was labeled with $\alpha$-$^{32}$P-dCTP using a Random Primer Labeling Kit (made by Takara Shuzo Co., Ltd.) to form a probe for isolating a clone.

(4) Isolation of an intended clone

The cDNA library obtained in (2) was spread on a total of 10 NZY plates (diameter 150 mm, made by Falcon) such that approximately 50,000 plaques were formed on one plate. Hyboind N+ (made by Amersham Corp.) which is a nylon filter was put on the plate, and immobilized with an aqueous solution containing 1.5M NaCl and 0.5N NaOH. Subsequently, prehybridization was conducted at 42° C. for 6 hours using the probe obtained in Step (3), and hybridization was further conducted at 42° C. for 12 hours.

Eleven clones were obtained in the first screening. These clones were spread on NZY plates (diameter 90 mm, made by Iwaki Glass K. K.) such that from 100 to 200 plaques were formed on one plate. Five clones were obtained in the second screening. *E. coli* XL1-Blue was infected with the obtained clones and Helper Phage R408 (made by Stratagene), EcoRI fragment inserted in the λZAPII was inserted in pBluescript SK(−), and this pBluescript SK(−) was introduced into *E. coli* XL1-Blue. Among the obtained clones, two clones each having an insert of approximately 3 kb were obtained.

(5) Determination of a base sequence of cDNA

In order to subclone one of the two clones each having the insert of approximately 3 kb as obtained in (4), deletion clones having various lengths were formed from the directions of the 5' side and 3' side of the cDNA insert. The deletion clone from the 5' side was cleaved with restriction endonucleases SacI and SpeI, and then digested with exonuclease III (made by Nippon Gene) from the SpeI site for from 1 to 10 minutes. The single-stranded cDNA was digested with Mung Bean Nuclease (made by Nippon Gene). The terminals thereof were completely smoothed with a Klenow fragment, and the product was cyclized with a T4DNA ligase, and introduced into *E. coli* HB101 strain. The deletion clone from the 3' side was cleaved with restriction endonucleases KpnI and HindIII, and then treated in the same manner as the deletion clone from the 5' side.

The base sequence was determined by the Sanger, et al deoxy termination method [Proc. Natl. Acad. Sci., U.S.A., 74, 5463–5467, (1977)] using an A. L. F. DNA Sequencer and an Auto Read Sequencing Kit (made by Pharmacia Co.).

Figure 2:
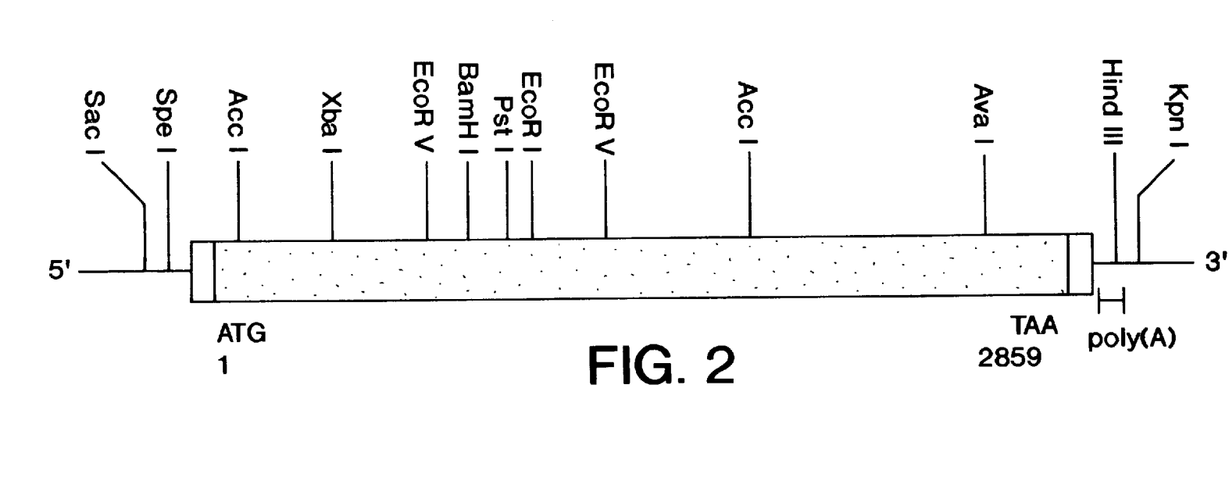
FIG. 2 shows a restriction endonuclease map of the cDNA encoding human 26S proteasome component P112 protein. A solid line shows pBluescript SK(−) which is a vector; a black column shows a translation region of cDNA encoding P112 protein; and white columns show 5' and 3' non-translation regions. The values under the columns show the first location of initiation codon ATG and the location of nucleotide which is 1 bp ahead of termination condon.

The base sequence of the above-obtained cDNA of P112 protein which is the component of human proteasome is represented by SEQ ID No: 2. The whole cDNA consisted of 3175 nucleotides, and the encoding region thereof consisted of 2859 nucleotides which corresponds to 953 amino acid residues. The amino acid sequence of P112 protein is represented by SEQ ID No: 1. The restriction endonuclease map of the cDNA of P112 protein which is the component of the human proteasome is shown in FIG. 2.

(6) Construction of an expression vector for P112 protein

The expression vector for P112 protein which is the component of the human proteasome was constructed in the following manner.

Figure 3:
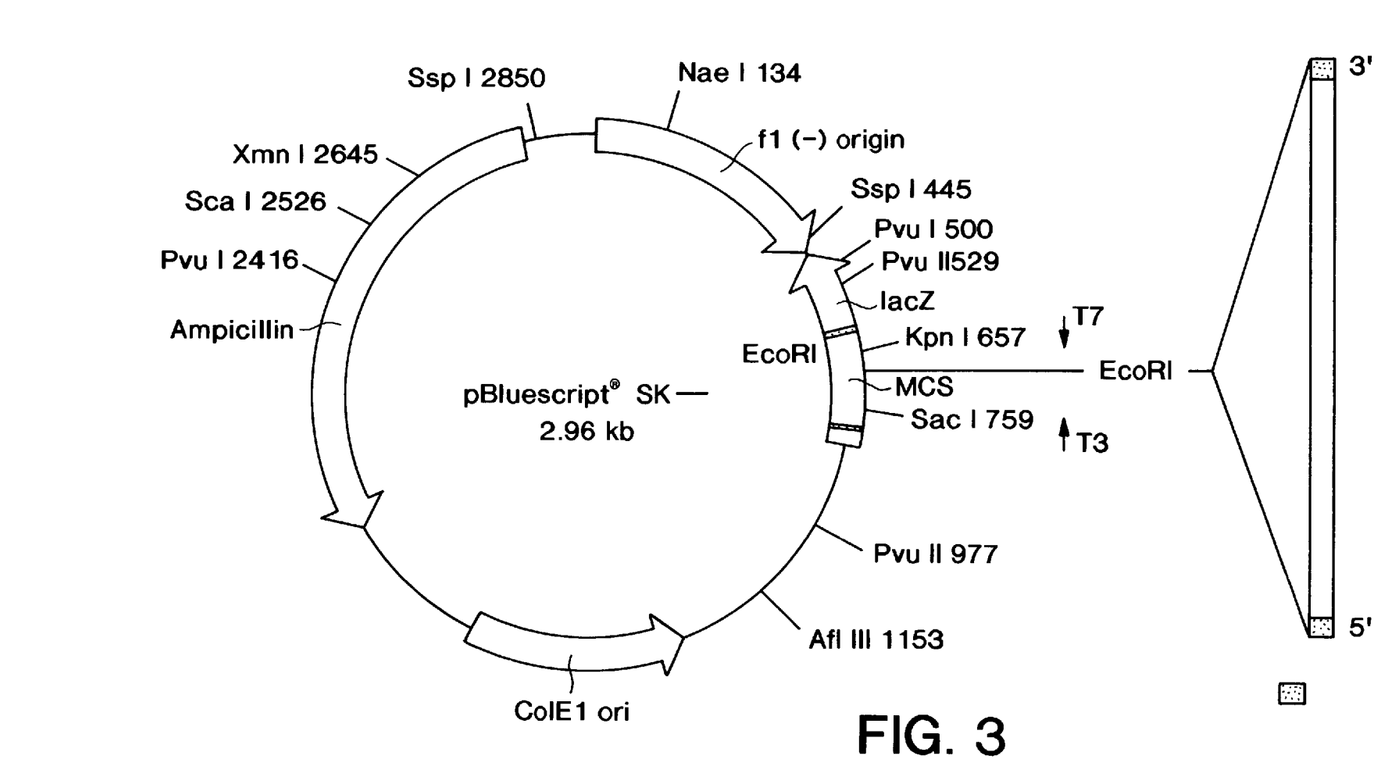
FIG. 3 shows structures of cDNA expression vectors for P112 protein and P31 protein which are components of human 26S proteasome.

PCR was conducted using a primer of a sense strand containing N-terminal methionine of the cDNA of P112 protein (5'-GAAGCTT ATGATCACCTCGGCCGCTGG-3') and a primer of an antisense strand containing AatII site located at 483 bp of the cDNA base sequence (5'-AAAGACGTCCAGTCTTCGTG-3'). The obtained PCR product encoding the N-terminal side of the cDNA of the P112 protein was phosphorylated with a T4 polynucleotide kinase, and completely smoothed with a Klenow fragment. The thus-obtained product was further digested with restriction endonuclease AatII. The thus-obtained digested-product was inserted by means of a T4DNA ligase into the pBluescript SK(−) which contains the cDNA original clone of the P112 protein, was digested with restriction endonucleases AatII and SmaI and had been dephosphorylated with a calf intestine alkaline phosphatase. The structure of the obtained CDNA expression vector for P112 protein is shown in FIG. 3. The expression vector was introduced into *E. coli* HB101 strain, and P112 protein was induced with isopropyl-1-thio-β-D-galactosidase in the cells. The accumulation of P112 protein in the cells was confirmed by the same reversed-phase HPLC and SDS-polyacrylamide electrophoresis as in Step (1).

EXAMPLE 2

The gene encoding P31 protein which is the component of the human proteasome was cloned in the same manner as in Example 1 except that a sense strand [5'-ATTTTTGAGATTGGTGC(G/T)CAGTGG(A/T)(G/T)TAT-3'] of XILEIGAQWSI (wherein X is an undetermined amino acid) and an antisense strand [5'-AGTCTTTCTAGTTC(G/T)GTGTGGAATTC(G/T)GC-3'] of XAEFHTELERL obtained by the determination of the partial amino acid sequence of P31 proteins were synthesized and used as primers. PCR was carried out using the single-stranded cDNA of HepG2 as a template in the same manner as in Example 1. Consequently, the PCR product of approximately 200 nucleotides was formed, and labeled with $\alpha$-$^{32}$P-dCTP using a Random Primer Labeling Kit (made by Takara Shuzo Co., Ltd.) in the same manner as in Step (3) of Example 1 to obtain a probe for isolating the clone.

Figure 4:
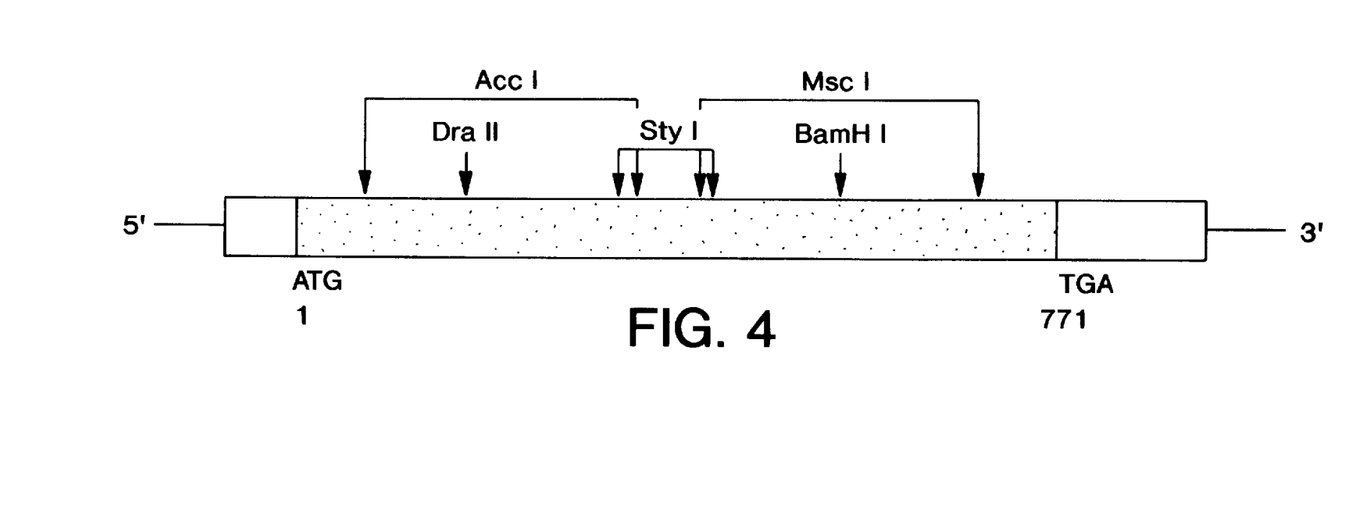
FIG. 4 shows a restriction endonuclease map of CDNA of human 26S proteasome component P31 protein. A solid line shows pBluescript SK(−) which is a vector; a black column shows a translation region of cDNA of P112 protein; and white columns show 5' and 3' non-translation regions. The values under the columns show the first location of initiation codon ATG and the location of nucleotide which is 1 bp ahead of termination codon.

The clone was isolated also in the same manner as in Step (4) of Example 1. As a result, 14 clones were obtained in the first screening. These clones were spread on NZY plates (diameter 90 mm) such that from 100 to 200 plaques were formed on one plate. Five clones were obtained in the second screening. *E. coli* XL1-Blue was infected with the obtained clones and Helper Phage R408 (made by Stratagene), EcoRI fragment inserted in the λZAPII was inserted into pBluescript SK(−), and pBluescript SK(−) was introduced into *E. coli* XL1-Blue. The base sequence of the thus-obtained product was determined. As a result, it is found that the cDNA of P31 protein is the component of the proteasome consisted of 928 nucleotides, and that the encoding region thereof consist of 717 nucleotides which corresponds to 257 amino acids. The base sequence of the cDNA encoding P31 protein is represented by SEQ ID No: 4, and the amino acid sequence of P31 protein is represented by SEQ ID No: 3. The restriction endonuclease map of the cDNA encoding P31 protein which is the component of the human proteasome is shown in FIG. 4.

The expression vector for P31 protein which is the component of the human proteasome was formed in the same manner as in Step (6) of Example 1. This expression vector was introduced into *E. coli* HB101 strain, and P31 protein was induced with isopropyl-1-thio-β-D-galactosidase in the cells. The accumulation of P31 protein in the cells was confirmed by the same reverse-phase HPLC and SDS-polyacrylamide electrophoresis as in Example 1.

What is claimed is:

1. A DNA comprising a DNA encoding the protein having an amino acid sequence of residues 2 to 953 defined in SEQ ID No: 1.

2. A DNA comprising a nucleotide sequence of residues 4 to 2859 defined in SEQ ID No: 2.

3. A recombinant vector into which the DNA as recited in claim 2 is inserted.

4. A recombinant vector into which the DNA as recited in claim 3 is inserted.

5. The recombinant vector of claim 4 which is p112 (FERM BP-4837).

6. A cell carrying the recombinant vector of claim 3, 4, or 5.

7. A DNA comprising a DNA encoding the protein having an amino acid sequence of residues 2 to 257 defined in SEQ ID No: 3.

8. A DNA comprising a nucleotide sequence of residues 4 to 771 defined in SEQ ID No: 4.

9. A recombinant vector into which the DNA as recited in claim 7 is inserted.

10. A recombinant vector into which the DNA as recited in claim 8 is inserted.

11. The recombinant vector of claim 12 which is p31 (FERM BP-4837).

12. A cell carrying the recombinant vector of claim 9, 10, or 11.

* * * * *

UNITED STATES PATENT AND TRADEMARK OFFICE
CERTIFICATE OF CORRECTION

PATENT NO. : 5,846,810

DATED : December 8, 1998

INVENTOR(S) : KEIICHI YANO, ET AL.

It is certified that error appears in the above-identified patent and that said Letters Patent is hereby corrected as shown below:

On the Title Page

AT [56] REFERENCES CITED

OTHER PUBLICATIONS

"GENBANK Locus No. T10004, Apr. 1994." should read --GENBANK Locus No. T10003, Apr. 1994.--.

COLUMN 2

Line 52, "CDNA" should read --cDNA--.

COLUMN 3

Line 60, "CDNA" should read --cDNA--; and
Line 61, "the" (second occurrence) should be deleted.

COLUMN 6

Line 3, "thus obtained" should read --thus-obtained--; and
Line 16, "Chirgwin, et al" should read --Chirgwin, et al.--.

UNITED STATES PATENT AND TRADEMARK OFFICE
CERTIFICATE OF CORRECTION

PATENT NO. : 5,846,810

DATED : December 8, 1998

INVENTOR(S) : KEIICHI YANO, ET AL.

It is certified that error appears in the above-identified patent and that said Letters Patent is hereby corrected as shown below:

<u>COLUMN 8</u>

```
Line 20, "CDNA" should read --cDNA--; and
Line 59, "consist" should read --consists--.
```

<u>COLUMN 19</u>

```
Line 31, "SEO" should read --SEQ--; and
Line 40, "(FERM BP-4837)" should read
        --(FERM BP-4838)--.
```

Signed and Sealed this

Twenty-second Day of May, 2001

Attest:

NICHOLAS P. GODICI

*Attesting Officer*     *Acting Director of the United States Patent and Trademark Office*